(12) United States Patent
Kiapour et al.

(10) Patent No.: US 12,318,125 B2
(45) Date of Patent: Jun. 3, 2025

(54) VARIABLE HEAD DRIVER FOR USE WITH SURGICAL IMPLANTS

(71) Applicant: Biofusion Management and Manufacturing, LLC, Austin, TX (US)

(72) Inventors: Ali Kiapour, Newton, MA (US); Rylan Reed, Austin, TX (US)

(73) Assignee: Biofusion Management and Manufacturing, LLC, Austin, TX (US)

( * ) Notice: Subject to any disclaimer, the term of this patent is extended or adjusted under 35 U.S.C. 154(b) by 398 days.

(21) Appl. No.: 17/985,508

(22) Filed: Nov. 11, 2022

(65) Prior Publication Data

US 2023/0084098 A1 Mar. 16, 2023

Related U.S. Application Data

(60) Provisional application No. 63/243,137, filed on Sep. 11, 2021.

(51) Int. Cl.
| | |
|---|---|
| *A61B 17/88* | (2006.01) |
| *A61B 17/70* | (2006.01) |
| A61B 17/00 | (2006.01) |
| A61F 2/30 | (2006.01) |

(52) U.S. Cl.
CPC ...... *A61B 17/8888* (2013.01); *A61B 17/7082* (2013.01); *A61B 17/8875* (2013.01); *A61B 2017/00486* (2013.01); *A61F 2002/30995* (2013.01)

(58) Field of Classification Search
CPC ........... A61B 17/7076; A61B 17/7082; A61B 17/7086; A61B 17/7091; A61B 17/8875; A61B 17/8888; A61F 2/4603; A61F 2002/4627
See application file for complete search history.

(56) References Cited

U.S. PATENT DOCUMENTS

| | | | |
|---|---|---|---|
| 11,950,821 B2 * | 4/2024 | Kaito | A61B 17/8615 |
| 2005/0033307 A1 * | 2/2005 | Cook | A61B 17/8888 606/104 |
| 2013/0150864 A1 * | 6/2013 | Marik | A61B 17/8888 606/104 |
| 2018/0235684 A1 * | 8/2018 | Hawkes | B25B 23/108 |

* cited by examiner

*Primary Examiner* — Larry E Waggle, Jr.
(74) *Attorney, Agent, or Firm* — Gregory Finch; Finch Paolino, LLC (57) ABSTRACT

An apparatus for use in placing an implant into a patient is disclosed. The apparatus features an outer assembly having an outer shaft with an expandable driving member at its distal end and an inner cannulated shaft that fits within and cooperates with the outer shaft to affect the driving member. The inner shaft includes an actuation knob attached to the proximal end of the inner shaft. A locking or driving thread is included on the outer surface of the inner shaft, proximal to the adjustment knob. The outer shaft includes a housing with the threaded interior such that when the inner shaft is mounted within the outer shaft, the driving thread operates with the threaded interior of the housing to allow for the inner shaft to be advanced along the inside of the outer shaft as the knob is turned. The tip of the inner shaft interacts with the interior of the driving member to expand the driving member.

5 Claims, 11 Drawing Sheets

VARIABLE HEAD DRIVER FOR USE WITH SURGICAL IMPLANTS

CROSS-REFERENCE TO RELATED APPLICATIONS

The present application claims the benefit of U.S. provisional application No. 63/243,137 filed Sep. 11, 2021, the contents of which are incorporated herein by reference in their entirety.

FIELD

The present application generally relates to an instrument used to place a surgical implant within a bone. In particular, the present application relates to a driver for placing a threaded implant within a patient the driver having improved fastening between the implant and driver.

BACKGROUND

Surgical procedures often employ implants that are placed within the patient to secure tissue such as bone. For example, a surgical implant is often used to fix a joint that no longer functions properly and as a result is causing discomfort in the patient. The implant, referred to as a fastener or fixation device, commonly comprises a head and a lead end positioned at the opposite ends of a shaft. The shaft includes a means to place and secure the fastener into tissues, for example threads. The head may include a variety of different receivers with different shapes and sizes depending upon the context of use.

A fastener or fixation device may be employed for the fixation of the sacroiliac or "SI" joint. In this procedure an elongated bone screw is utilized. During this procedure, it is important to properly insert the bone screw to ensure implant stability and close contact with the bone. In addition, it is important to ensure proper placement of the bone screw to ensure in-growth on the bone into the implant. Many bone screws include features that allow the bone into which they have been placed to grown into the screw such as a roughened surface and windows.

During a surgical procedure, the head of the bone screw is engaged by an instrument that is used to drive the screw into the bone. In many cases the instrument resembles a common screwdriver, but the similarities often end with appearance as dictated by function. In particular, the screwdriver contains specially adapted features for medical applications. A surgical driver includes a specialized tip that engages the receiver of an implant such that as the instrument is rotated, the fastener is driven into the tissue.

To lower the cost of surgical procedures instruments such as a driver are sterilized and re-used. But fixing an SI joint can be technically difficult given the desire to limit the size of the incision giving access to the treatment site. There is deep operative exposure that the screwdriver and screw complex must navigate that can place strain on the instrument. Despite this, the screw must be held firmly into place to prevent detachment which can result in complicating the procedure. Many drivers feature self-retaining features that hold the screw in place. In addition, there are articulating drivers that can lock the screw in place. The operation of these types of drivers proves complicated, however, as such a driver has multiple moving parts.

After multiple uses, a driver is subject to wear and tear which has deleterious effects on performance. Drivers with multiple and complex components experience greater malfunction rates and are difficult and overly expensive to repair. This can result in the instrument being discarded and expense incurred with providing and entirely new one. In addition, the retaining features at the tip of the driver can deform and damage over repeated use resulting in a loose attachment to the screw which often results in screw falling from the driver into the surgery site during the surgical intervention.

Therefore, what is needed is a device capable of providing a secure fit between the screw head and the screwdriver without a complex assembly to accomplish this fit.

SUMMARY

An apparatus for use in placing an implant into a patient is disclosed. The apparatus generally comprises an outer assembly having an outer shaft with a driving member at its distal end and an inner cannulated shaft that fits within and cooperates with the outer shaft to affect the driving member.

The inner shaft includes a cannula along its length which allows for further instrumentation such as guidewires to be passed therethrough to the surgical site. An actuation knob is attached to the proximal end of the inner shaft. A locking or driving thread is included on the outer surface of the inner shaft, proximal to the adjustment knob. The distal tip of the inner shaft is tapered and is utilized for affecting the outer diameter of the tip of the outer shaft.

The outer assembly includes a quick connect adapter at is proximal end that can link with a variety of handles. The outer shaft is cannulated along its longitudinal axis such that the inner housing may be placed therein. A knob housing is positioned between the adapter and the outer shaft. This housing is hinged such that it can open allowing the inner shaft to be passed into the outer shaft. Once the inner shaft is placed within the outer shaft, the housing is closed and a locking feature on the housing retains the inner shaft within the outer shaft. The housing is open ended such that the actuation knob can be accessed and turned during a surgical procedure.

A drive housing is connected to and located next to the knob housing of the outer shaft on the opposite side form the quick connect adapter. The second housing has an inner threaded surface and engages the locking or driving threaded of the inner shaft. An expandable driving member is located at the distal end of the outer shaft and is shaped to engage a driver receptacle of a surgical implant. The distal tip has a tapered inner diameter that matches the taper of the inner shaft.

Once the inner shaft is placed within the cannula of the outer shaft the knob is rotated. The tapered tip of the inner shaft advances toward the distal tip of the outer shaft. This causes the tip of the inner surface to impinge upon the inner tapered diameter of the outer shaft and expands the driving member fixing the member firmly within the driver receptacle of the surgical implant.

The foregoing has outlined rather broadly the more pertinent and important features of the device so that the detailed description that follows may be better understood. Additional features will be described hereinafter which form the subject of the claims of the invention. It should be appreciated by those skilled in the art that the conception and the disclosed specific methods and structures may be readily utilized as a basis for modifying or designing other structures for carrying out the same purposes of the device. It should be realized by those skilled in the art that such equivalent structures do not depart from the spirit and scope of the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Figure 1:
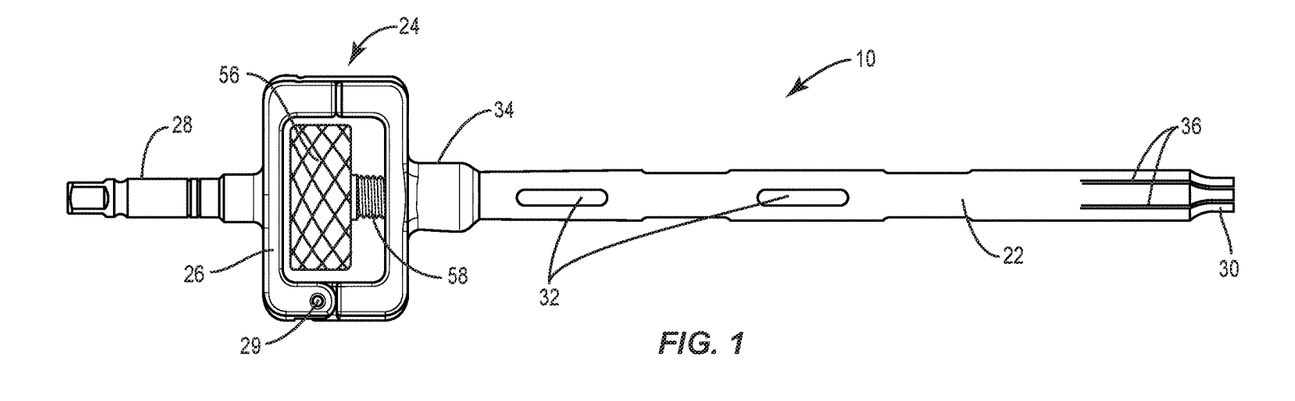
FIG. 1 is a side view of the variable head driver.
Figures 1A, 1B:
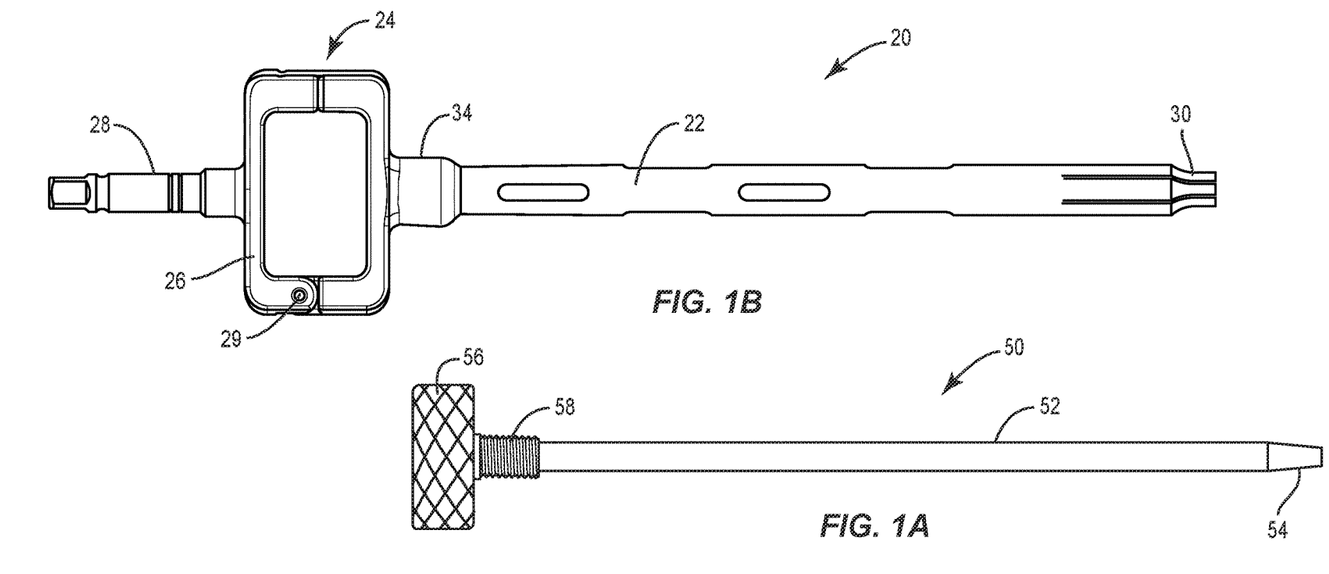
FIG. 1A is a side view of the inner shaft of the variable head driver.
FIG. 1B is a side view of the outer shaft of the variable head driver.
Figures 2, 2A:
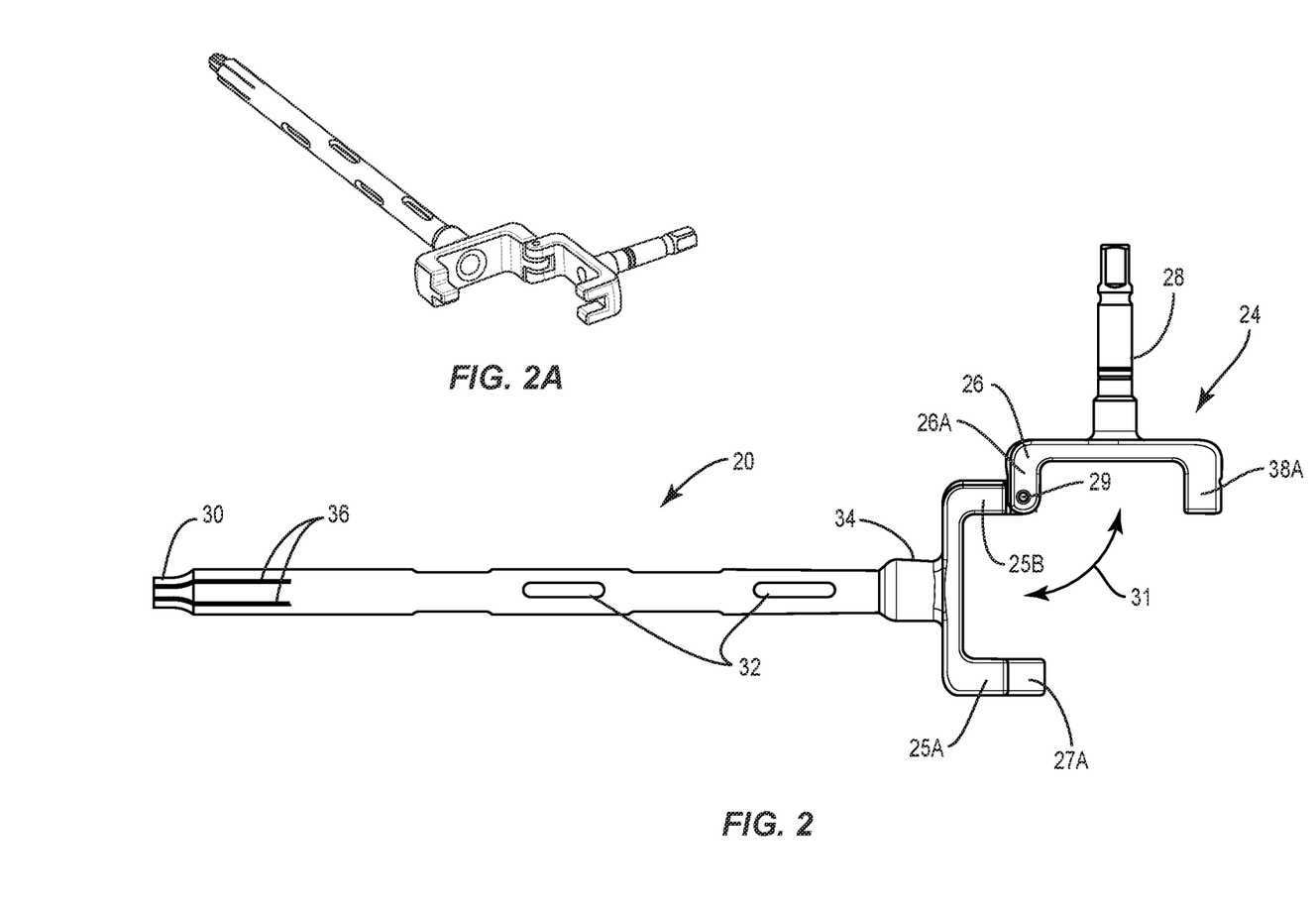
FIG. 2 is a side view of the outer shaft of the variable head driver illustrating the expansion housing in an open position.
FIG. 2A is an oblique view of the outer shaft of the variable head driver.

FIGS. 1-1B illustrates the expandable driver 10 of the present application. The driver 10 presents an advantage over present designs as its assembly, described in detail below, has fewer components. In the event of damage of a component, the damage part can be easily replaced. In addition, the driver 10 allows for easy removal of components for cleaning and sterilization. The driver 10 has an outer assembly 20 and in inner assembly 50. Driver 10 may be constructed from ultra-high anti-rust & high-hardness stainless steel, titanium, titanium alloy, or high anti-rust stainless steel. The material selected will allow for sterilization and multiple reuses.

The driver comprises an outer assembly 20 and inner assembly 50. Outer assembly 20 includes an outer elongated shaft 22 with a driving member 30 at its distal end. Driving member 30 has an inner surface that is tapered to match the contour of tip 54 of inner shaft 52. The shaft 22 is cannulated allowing for the passage of an inner cannulated shaft 52 of inner assembly 50 through its entire length. As will be described in further detail below, inner shaft 52 cooperates with outer shaft 22 to expand the driving tip 30.

Figure 3:
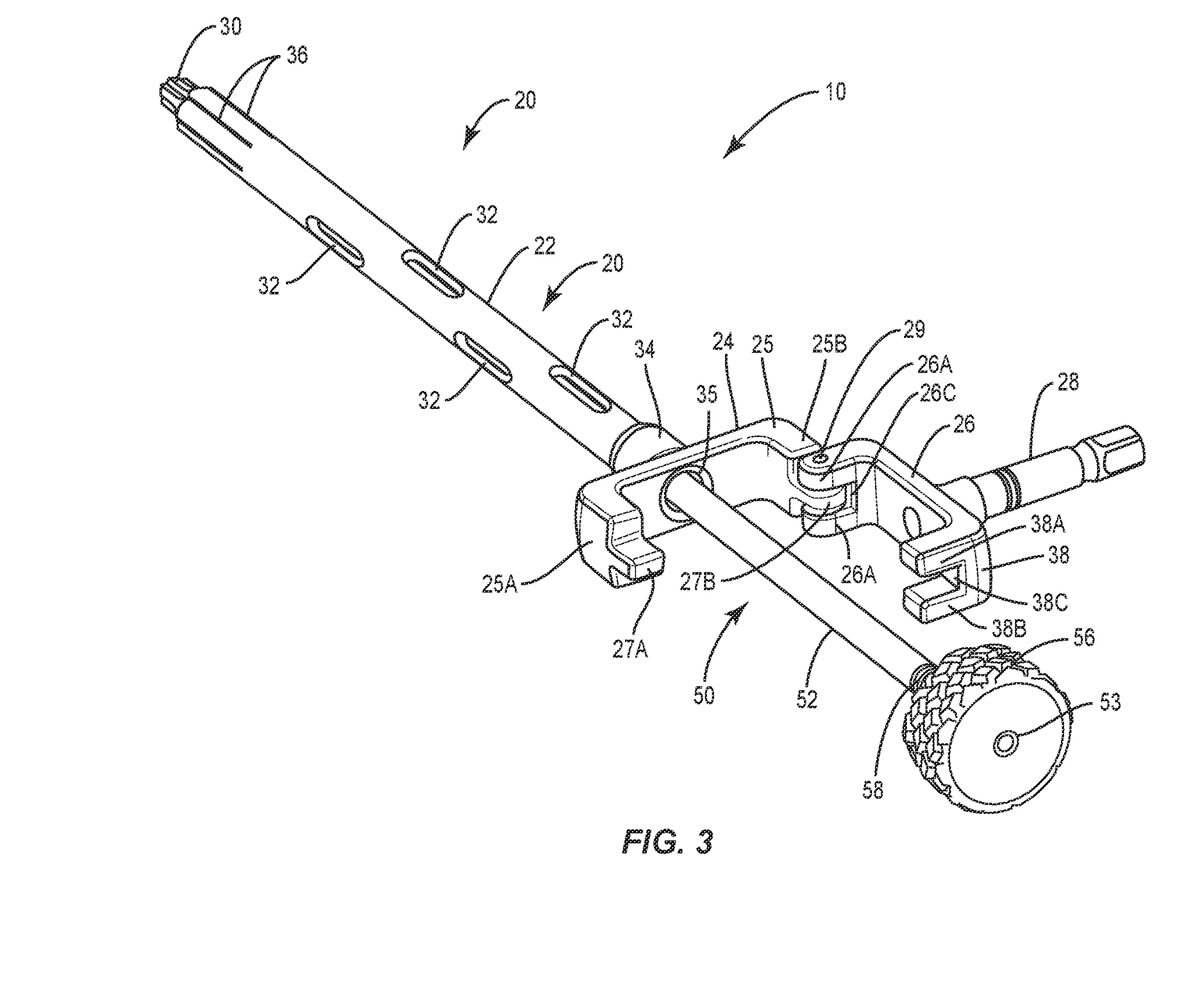
FIG. 3 is an oblique view of the variable head driver showing the inner shaft partially positioned within the outer shaft.

As shown in FIGS. 1A and 3 the inner assembly 22 comprises an elongated shaft 52. Shaft 52 has an actuation knob 56 at its proximal end and a tapered tip 54 at its distal end. The knob 56 is preferably textured and allows for easy articulation when inner assembly 50 is in situ within outer assembly 20. The inner shaft 52 includes a cannula 53 along its length which allows for further instrumentation such as guidewires to be passed therethrough to the surgical site. A locking or driving thread 58 is included on the outer surface of the inner assembly 50 between the adjustment knob 56 and the inner shaft 52. The distal tip 54 of the inner shaft is tapered and is utilized for affecting the outer diameter of the tip 30 of the outer shaft 22.

As shown in FIG. 1B the outer assembly 20 includes a quick connect adapter 28 at is proximal end that can link with a variety of handles such as a square or T-handle. The outer assembly comprises an outer elongated shaft 22, and knob housing 24 and an adjustment housing 34. Adjustment housing 34 is fixedly mounted between shaft 22 and knob housing 24 and as shown in FIG. 3 includes and inner threaded surface 35.

Outer shaft 22 has a cannula along its longitudinal axis such that accommodates inner shaft 52. The distal end of shaft 22 includes an expandable driving member 30. Driving member has laser cut slots 36 that run toward the proximal end of shaft 22 terminating just behind tip 30. Tip 30 cooperates with the driven end of a surgical implant 60, described in detail below with reference to FIGS. 7-10. Tip 30 may comprise single slot, cruciform, Philipps, hex, star, or as illustrated, a torx head that matches the driven end of a surgical implant.

A knob housing 24 is positioned between the adapter 28 and the outer shaft 22. As shown in FIG. 3, the housing 24 is hinged such that it can open allowing the inner shaft 52 to be passed into the outer shaft 22. Knob housing 24 include a first side 25 and a second or hinged side 26. First side 25 includes two wings 25A, 25B with a locking extension 27A and hinge extension 27B protruding therefrom. Second side 26 includes an upper hinge extension 26A and a lower hinge extension 26B. Second side 26 also includes a mating section 38 with upper 38A and lower 38B extension.

Figure 4:
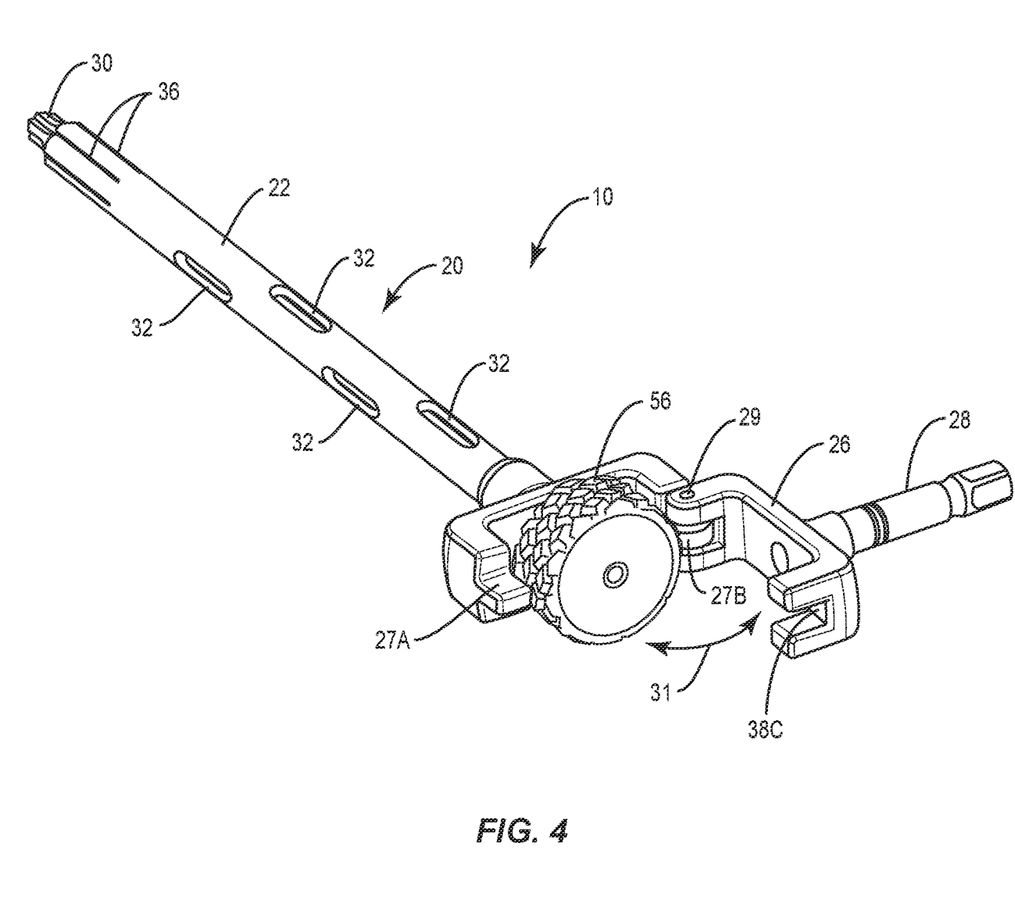
FIG. 4 is an oblique view of the variable head driver showing the inner shaft positioned within the outer shaft.
Figure 5:
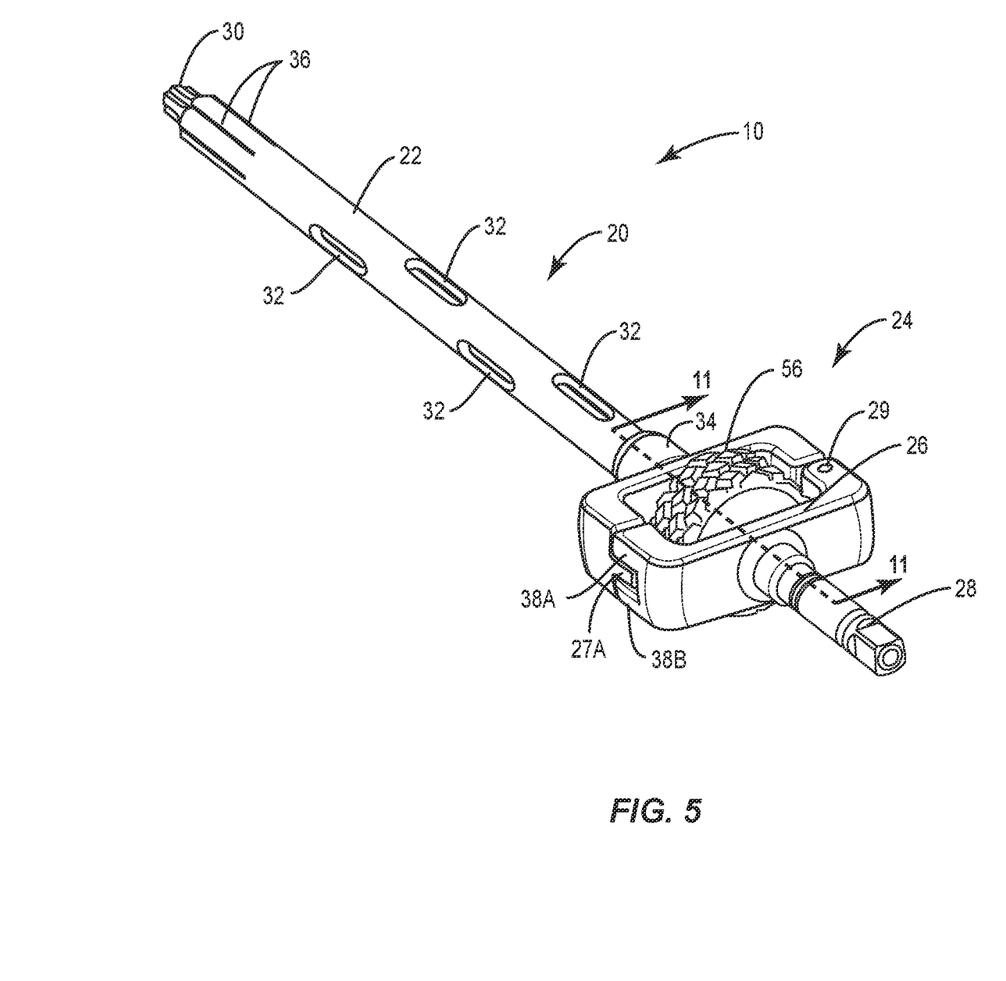
FIG. 5 is an oblique view of the variable head driver showing the inner shaft positioned with the outer shaft and the knob housing closed and locked.

As can be seen in FIGS. 3 and 4, the extensions 26A, 26B, 38A and 38B are spaced apart such that an opening 26C is defined between 26A and 26B and an opening 38C between 38A and 38B. As shown in FIGS. 3 and 4 when assembled, the hinge extension 27B of the first side 25 fits between opening 26C. A hinge pin 29 is placed through an aperture in 26A, 27B and 26B forming the hinge which allows hinge side 26 of knob housing 24 to swing in the direction of arrow 31. As shown in FIG. 5, when swung into a closed position locking extension 27A fits between upper and lower extensions 38A and 38B. Locking extension 27A has a slightly tapered cross section that is larger than opening 38C such that extension is releasably retained within opening 38C.

Figure 12A:
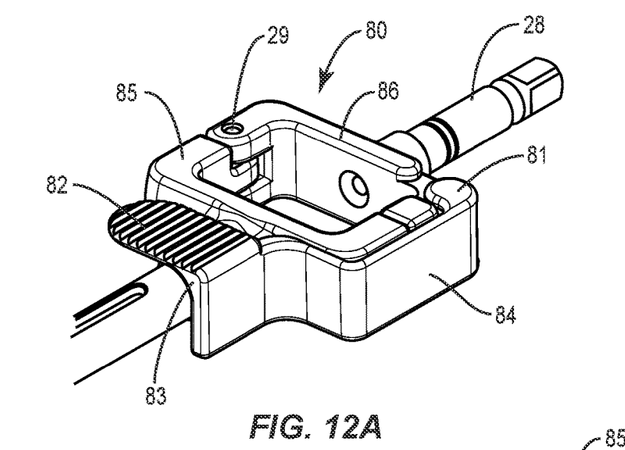
FIG. 12A is a perspective view of an alternate embodiment of the expansion knob housing of the variable head driver.
Figure 12B:
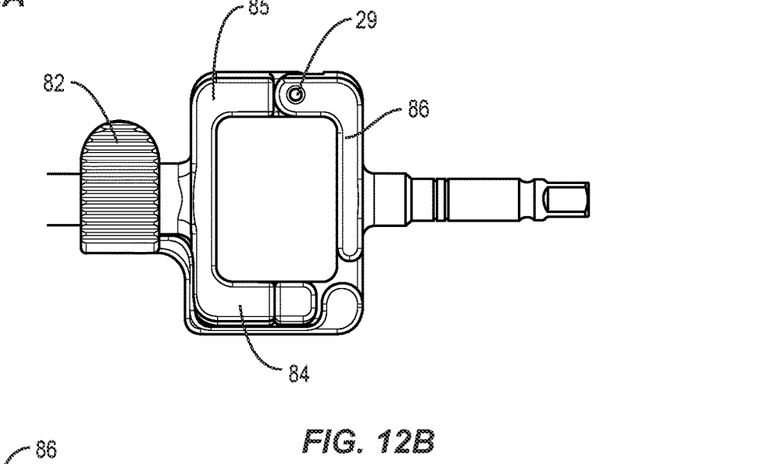
FIG. 12B is a top view of the embodiment of FIG. 12A.
Figure 12C:
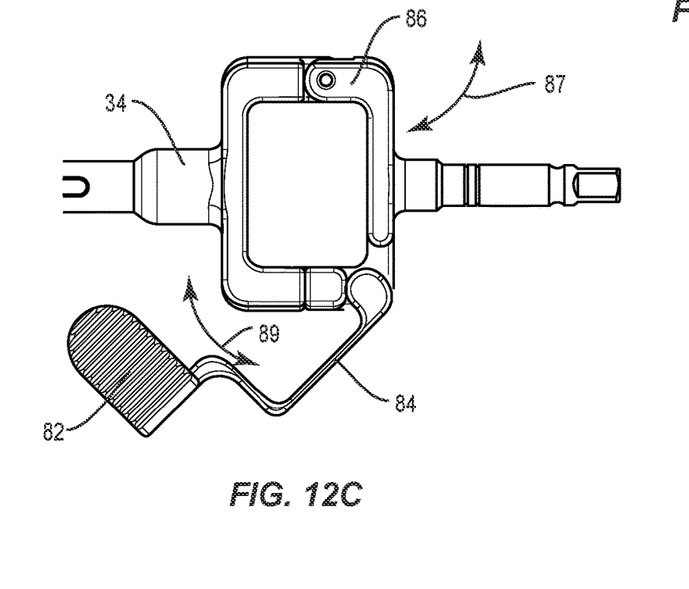
FIG. 12C is a top view of the embodiment of FIG. 12A.

FIG. 12A-C illustrates and alternate embodiment of the knob housing 24. As shown in FIG. 12A, knob housing 80 is constructed substantially as described above and has a first side 85 and a second or hinged side 86 which rotates in the direction indicated by arrow 97, shown in FIG. 12C, to effectuate opening and closing of the housing 80. A locking plate 84 is attached to second side 86 via a hinge 81. Lock plate 84 includes a treaded locking member 82 which has an underside 83 that is contoured to tightly fit about the outside of outer adjustment housing 34. When the hinged or second side 86 of housing 80 is in a closed position as shown in FIG. 12A, locking plate 84 is swung in the direction of arrow 89 such that the inner surface 83 fits securely about the outside of adjustment housing 34. This locks the first 85 and second 86 side of housing 80 into place. When tread 82 is pressed its inner surface 83 deforms and disengages from housing 34 allowing locking plate 84 to be swung open. The second side 86 is free to swing open as described above opening housing 80.

Figure 13A:
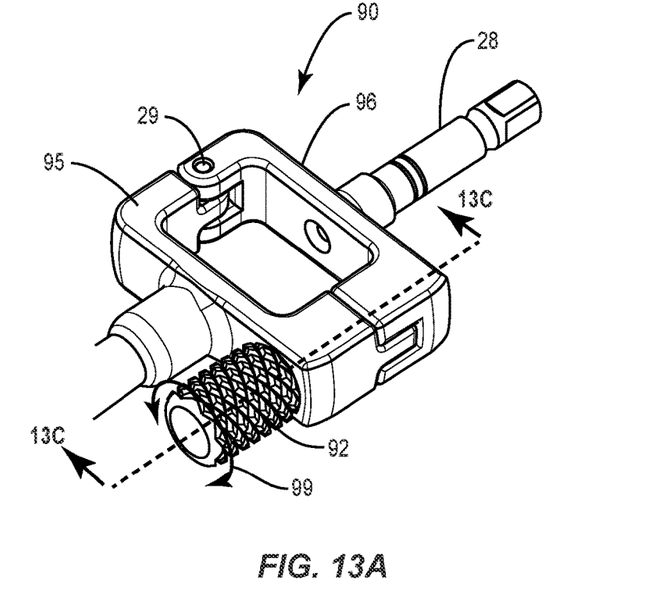
FIG. 13A is a perspective view of yet another alternate embodiment of the expansion knob housing of the variable head driver
Figure 13B:
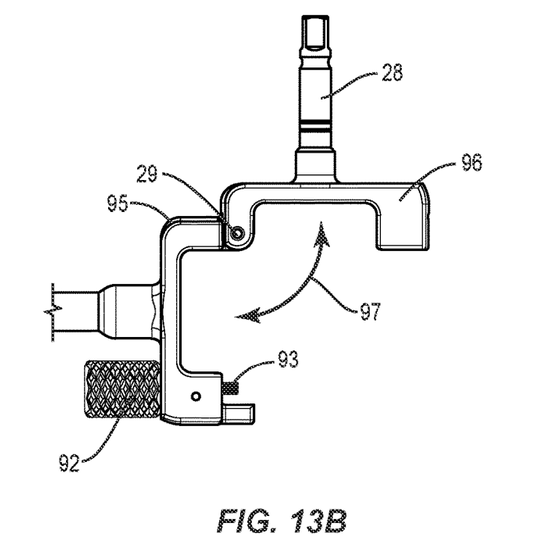
FIG. 13B is a top view of the embodiment of FIG. 13A.
Figure 13C:
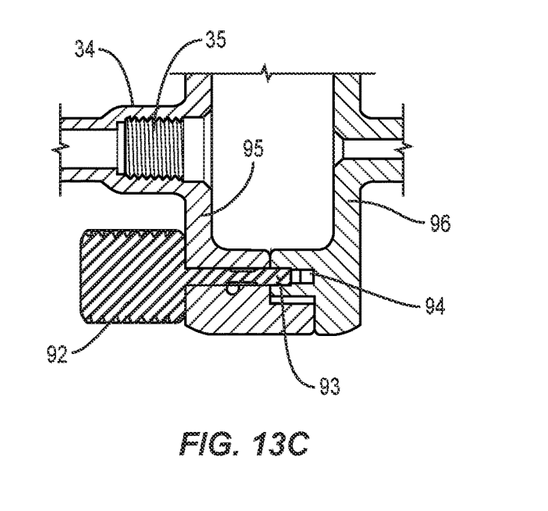
FIG. 13C is a view taken along line C-C of FIG. 13A.

FIG. 13A-C illustrates another alternate embodiment of the knob housing. As shown in FIG. 13A, the housing 90 includes a first 95 and second or hinged side 96 and is constructed substantially as described above. The second side 96 rotates about hinge 29 in the direction of arrow 97 to open housing 90 allowing inner shaft 52 to be placed in outer shaft 22 as described above.

As shown in FIGS. 13B and 13C, a rotating or threaded locking member 92 is mounted on first side 95 of housing 90. The first side 95 includes an aperture 100 through which locking member 92 extends. The mid-section of the locking member 92 includes slots 98 along its length. The slots 98 allow retaining pin 9, mounted within side 95, to fit therein such that the travel of locking member 92 in direction 101 is restricted thus retaining locking member 92 within aperture 100. The distal end 93 of locking member 92 is threaded and fits within a threaded opening 94 in second side 96.

When first side 95 and second side 96 of housing 90 are in a closed position, the knob 102 of locking member 92 may be rotated as indicated by arrow 99, such that the threaded distal end 93 is secured within threaded opening 94, locking the first 95 and second 96 sides of housing 90 together. The process is reversed such that the threaded member 93 is disengaged from opening 94 allowing locking member to travel in the direction of arrow 101. The housing 90 is then in an unlocked position and may be rotated open in the direction indicated by arrow 97.

The assembly of the components of driver 10 can be described with reference to FIGS. 3-6. As shown in FIG. 3, the hinge side 26 of knob housing 24 is opened. As shown in FIG. 3, the tip 54 of the inner shaft 52 is inserted into the cannula of outer shaft 22, and inner shaft 52 is advanced distally along the inside of outer shaft 22. The progress of the advancement of the inner shaft can be seen through viewing panes 32 arrayed along outer shaft 22. As shown in FIG. 4, the inner shaft 22 is advanced until the driving thread 58 is in contact with the housing threads 35. Adjustment knob 56 is turned clockwise threading the driving thread 58 into the housing threads 35. As shown in FIG. 5, once the inner shaft 52 is placed within the outer shaft 22 and initial threading is complete, the hinge side 26 of knob housing 24 is swung closed in the direction of arrow 31 of FIG. 4 locking the inner shaft 22 within outer shaft 22 and knob 56 within housing 24.

Figure 6:
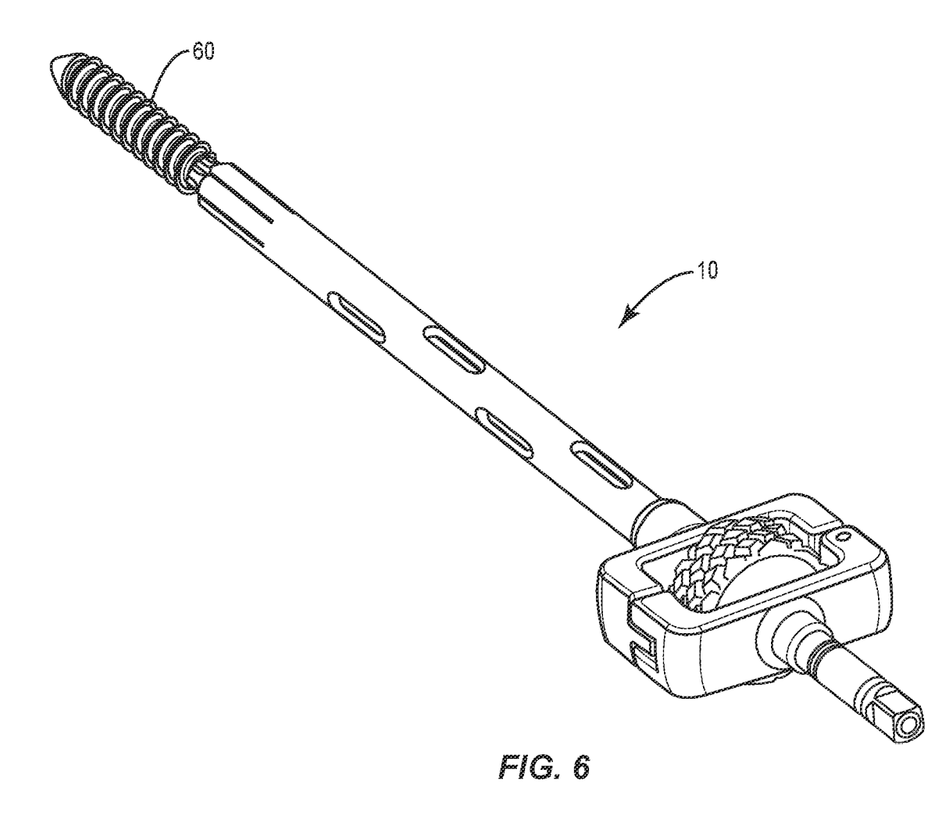
FIG. 6 is an oblique view of the variable head driver showing a surgical implant mounted at the distal tip.

FIG. 6 shows the assembled driver 10 with an example of a surgical implant 60 that can be mounted on the driving member 30. FIGS. 7-10 illustrate the action of the tip 54 of inner shaft 52 as it interacts with the inner portion of driving member 30 and the driving member's 30 interaction with the driven end 64 of the implant 60.

Figure 7:
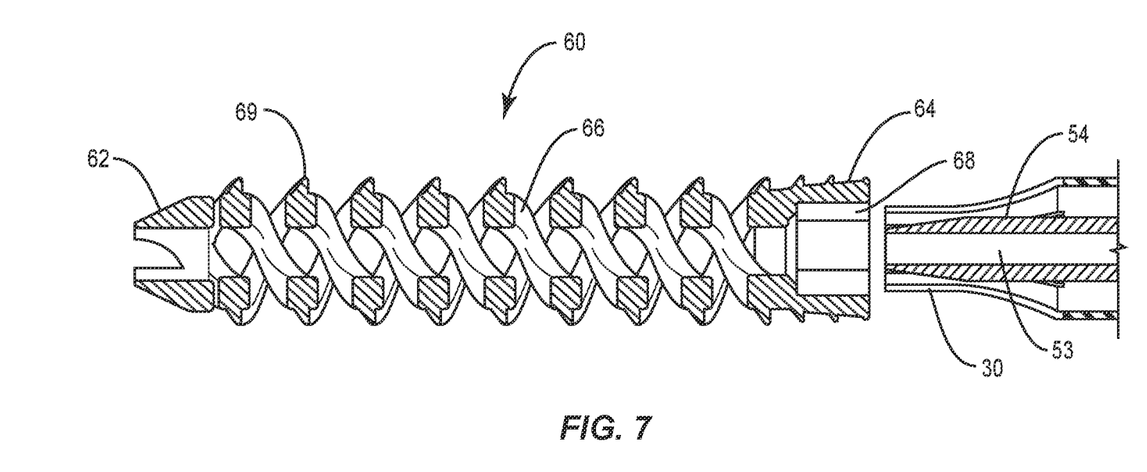
FIG. 7 is a side view of an exemplary surgical implant with the expandable driving member placed within its driven end.
Figure 8:
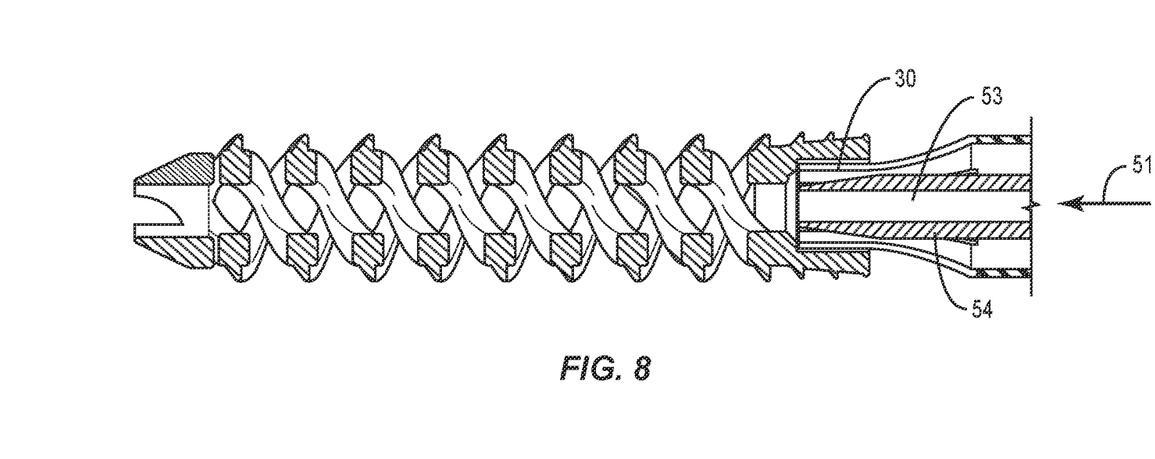
FIG. 8 is a side view of an exemplary surgical implant with the expandable driving member placed in the driven end.
Figure 9:
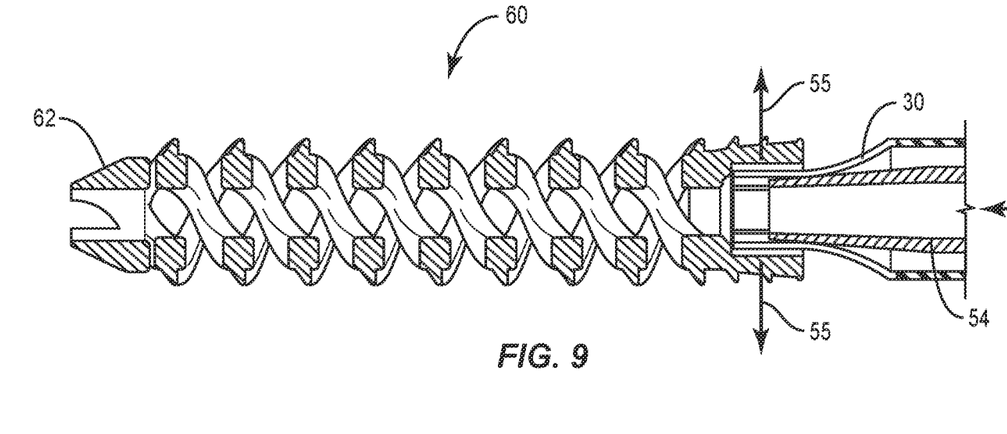
FIG. 9 is a side view of an exemplary surgical implant with the expandable driving member placed in the driven end.

As shown in FIG. 7, the tapered tip of inner shaft 52 is positioned proximal to the inner section of driving member 30. The driving member 30 is shown outside the driver receptacle 68 of implant 60. In FIG. 8, the driving member 30 is positioned within receptacle 68. In many of the existing driver or an external grip on the driven end 64 of the implant 60. These designs ultimately fail as the wear of repeated use dissipates their efficacy. As shown in FIG. 9, the tapered tip 54 of the inner shaft 52 is advanced distally in the direction of arrow 51. As tip 54 is advanced it interacts with the inside of driving member 30 and causes it to expand in the direction of arrow 55.

Figures 10, 10A:
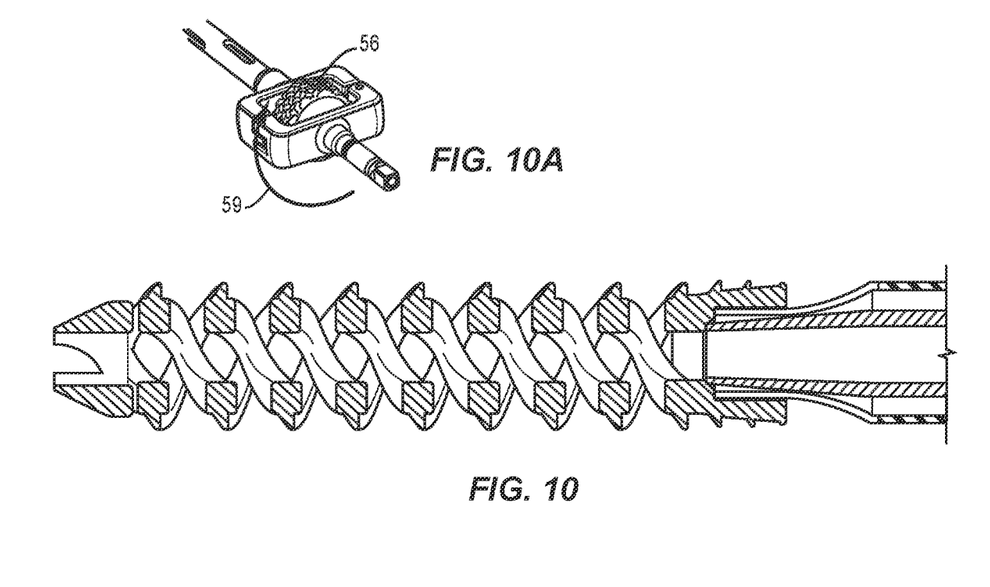
FIG. 10 is a side view of an exemplary surgical implant with the expandable driving member placed in the driven end.
FIG. 10A is a perspective view of the proximal end of the variable head driver.
Figure 11A:
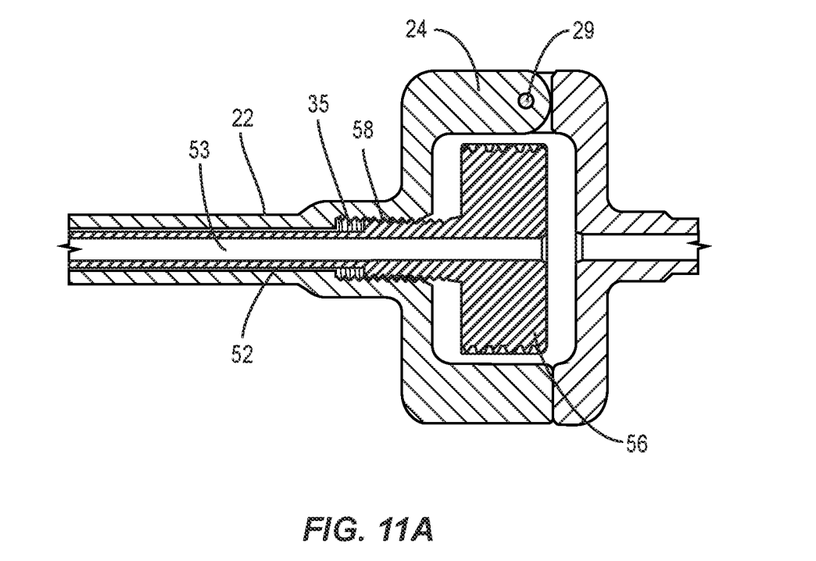
FIG. 11A is a sectional view of the knob housing along the line 11-11 of FIG. 5 showing the inner shaft in an unlocked position.
Figure 11B:
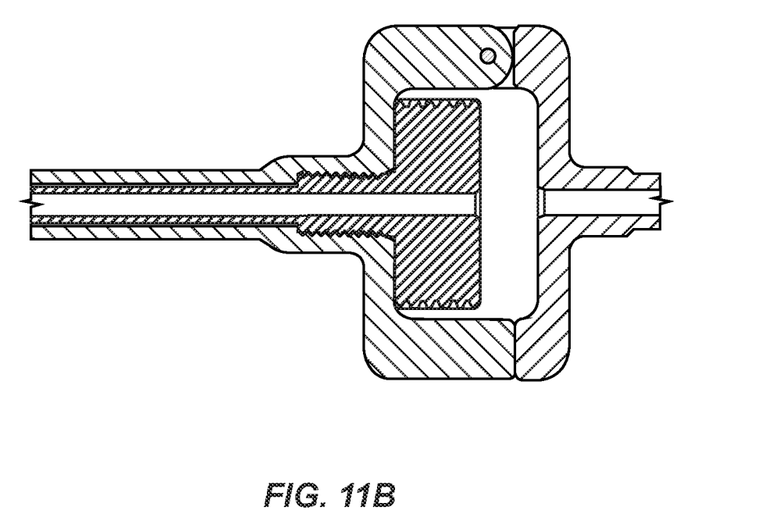
FIG. 11B is a sectional view of the knob housing along the line 11-11 of FIG. 5 showing the inner shaft in a locked position.

As shown in FIG. 10, once the tip 54 is fully advanced, the driving member 30 is fully secured with the driver receptacle 68 of implant 60. The advancement of the tip 54 is accomplished by actuating the adjustment knob 56 forcing the interaction of the adjustment or driving thread 58 with the housing thread 35. As shown in FIG. 10A, as the knob 56 is turned in the direction of arrow 56 tip 54 advances. FIGS. 11 and 11A shows the knob in a position that corresponds to the position of the tip 54 seen in FIG. 7. FIG. 11A shows the knob 56 rotated fully such that the tip 54 is in a locked position and the driving member 30 is fully expanded and secure within driver receptacle 68.

Once fully secure within driver receptacle 68, the driver 10 can be actuated to drive threads 69 of implant 68 into the desired location of the patient. When implantation is complete, knob 56 is turned in a counter direction to arrow 56 and the implant 60 is released from driver 10. The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

DRIVER WITH VARIABLE HEAD FOR BONE IMPLANT

Drawing Element List

10. Expandable Driver
12.
14.
16.
18.
20. Outer Housing Assembly
22. Outer Shaft (Cannulated)

24. Expansion Knob Housing
25. First Side of Expansion Knob Housing
25A Receptacle of 25
25B Hinge of 25
26. Hinged Side/Second Side
26A Upper Hinge Extension
26B Lower Hinge Extension
27A Locking Extension
27B Hinge Extension
28. Quick Connect/Proximal End
29 Hinge Pin
30. Driving Member/Distal End
31. Arrow (illustrating opening)
32. Viewing Panes
34. Outer Adjustment Housing
35. Housing Threads
36. Slots
38. Mating Extension
38A Top Wing of 38
38B Bottom Wing of 38
50. Inner Assembly
51. Arrow (Inner Shaft Moving)
52. Inner Shaft (Cannulated)
53. Cannula of Inner Shaft
54. Tapered Tip (Distal)
55. Arrow (Tapper Tip Expansion)
56. Adjustment Knob
58. Driving Locking/Adjustment Thread
60. Implant
62. Leading End
64. Driven End
66. Cannula of Screw
68. Driver Receptacle
69. Threads of Implant

What is claimed is:

1. An apparatus for use in implanting a surgical implant comprising:
    an adapter for attaching a handle thereto;
    an outer assembly having
        an outer shaft with a cannula through its length;
        a hinged housing located at a proximal end of the outer shaft;
        an adjustment housing located next to the hinged housing of the outer shaft, the adjustment housing having an inner threaded surface; and
        an expandable driving member located at a distal end of the outer shaft, said expandable driving member being shaped to engage a driver receptacle of a surgical implant and having a tapered inner diameter;
    an inner shaft having
        a cannula through its length;
        an actuation knob at its proximal end;
        a driving thread near distal to the actuation knob; and
        a tapered tip at its distal end,
    wherein said inner shaft is placed within the cannula of the outer shaft such that said driving thread of the inner shaft engages the inner threaded surface of the outer shaft and said actuation knob is located within the hinged housing such that turning the actuation knob advances the inner shaft in a distal direction within the outer shaft.

2. The apparatus of claim 1 wherein the hinged housing comprises a first side fixedly mounted to the outer shaft, said first side having a first extension and a second extension protruding perpendicularly from the first side.

3. That apparatus of claim 2 wherein the hinged housing further comprises a second side hinged to the first side, said second side having a first extension and a second extension protruding perpendicularly from the second side.

4. The apparatus of claim 3 wherein the first and second extensions of the second side are bifurcated forming an opening between a top of the extensions and a bottom of the extensions.

5. The apparatus of claim 4 wherein the first extension of the first side fits in the opening between the top and bottom of the first extension of the second side, said extension of the first side and the top and bottom of the extension of the second side being adapted to have a hinge pin placed therethrough.

\* \* \* \* \*